United States Patent [19]

Lindauer et al.

[11] Patent Number: 4,627,934

[45] Date of Patent: Dec. 9, 1986

[54] SINGLE PHASE CLEAR LIQUID AFTER-SHAVE TREATMENT PRODUCT CONTAINING ALOE VERA

[75] Inventors: Jerome I. Lindauer, Hillsdale, N.J.; Sharon L. Reich, Briarwood, N.Y.

[73] Assignee: International Flavors & Fragrances Inc., New York, N.Y.

[21] Appl. No.: 695,074

[22] Filed: Jan. 25, 1985

[51] Int. Cl.$^4$ .............................................. A61K 7/46
[52] U.S. Cl. ............................ 252/522 R; 424/195.1; 514/390
[58] Field of Search .................... 252/522 R; 514/390; 424/195.1

[56] References Cited

U.S. PATENT DOCUMENTS

| | | | |
|---|---|---|---|
| 1,167,230 | 1/1916 | Tambach | 424/195.1 |
| 3,681,090 | 5/1984 | Maughan | 99/149 R |
| 3,878,197 | 4/1975 | Maret | 424/195.1 |
| 4,302,443 | 11/1981 | deNavarre et al. | 424/195.1 |
| 4,369,180 | 1/1983 | Mihalovits | 424/195.1 |
| 4,446,131 | 8/1972 | Huth | 424/195 |

FOREIGN PATENT DOCUMENTS 55-104205  9/1980  Japan ................................ 424/195.1

OTHER PUBLICATIONS

Eldred et al, Chem. Abst., vol. 1, p. 85, #2.
Mecca, "Proceedings of the Scientific Section of the Toilet Goods Assn.", #23 (1955).
Mecca, "Proceedings of the Scientific Section of the Toilet Goods Assn.", #31, (1959).

*Primary Examiner*—James H. Reamer
*Attorney, Agent, or Firm*—Arthur L. Liberman

[57] ABSTRACT

Described is a single phase clear hydroalcoholic aftershave treatment product containing aloe vera and, optionally, allantoin and a process for preparing same comprising the steps of:
(a) either forming:
   (i) aloe vera gel; or
   (ii) a product resulting from steam distilling aloe vera leaves and separating the resulting oil phase from the resulting aqueous phase;
(b) extracting the oil-miscible aloe vera fraction from the organic phase of the steam distillation product or from the aloe vera gel by intimately admixing therewith a quantity of extraction solvent and physically separating the extract phase from the raffinate phase;
(c) separating the extraction solvent from the oil-miscible aloe vera extract phase by means of fractional distillation;
(d) intimately admixing the resulting distilled oil-miscible aloe vera phase with a totally miscible perfume oil;
(e) admixing the resulting mixture with a polyalkylene glycol, a polyalkylene glycol alkyl ether, a quaternary ammonium salt, a lanolin oil-polyalkylene glycol reaction product, water and, optionally, allantoin or an allantoin-aluminate complex, with the amount of water being in the range of from about 30% up to about 50% by weight of the total mixture.

1 Claim, 3 Drawing Figures

SINGLE PHASE CLEAR LIQUID AFTER-SHAVE TREATMENT PRODUCT CONTAINING ALOE VERA

BACKGROUND OF THE INVENTION

This invention relates to a single phase clear hydroalcoholic after shave treatment composition containing aloe vera and, optionally, allantoin and a process for preparing same.

Both allantoin and extracts from the aloe vera plant have been utilized either separately or in combination in various cosmetic and toiletry products. The attributes and efficacy of these ingredients have been exploited as is evidenced in the prior art, for example:

S. B. Mecca, "The Healing, Skin-Softening and Tissue-Building Action of Allantoin" Drugs and Allied Industries, July, 1960

S. B. Mecca, "Allantoin In Cosmetic Formulations" Proceedings of the Scientific Section of The Toilet Goods Association, No. 23, May 1955

Danhof, et al, "Stabilized Aloe Vera: Effect On Human Skin Cells", Drug and Cosmetic Industry, August 1983, page 52

"Aloe Vera, 'Ageless' Botanical", Soap/Cosmetic/Chemical Specialties, February 1977, page 34

Leung, "Aloe Vera In Cosmetics", Drug and Cosmetics Industry, June 1977, page 34

Mortin "Folk Uses And Commercial Exploitation of Aloe Leaf Pulp", Economic Botany, Volume 15, No. 4, pages 311-319, October-December 1961

Gjerstad, "An Appraisal of the Aloe Vera Juice", American Perfumer And Cosmetics, Volume 84, May 1969, page 43

S. B. Mecca, "Allantoin and the Newer Aluminum Allantoinates" Proceedings of the Scientific Section of the Toilet Goods Association, No. 31, May, 1959 (of specific interest is the disclosure therein of the after shave lotion, to wit:

"... Ingredients | Weight Percent
---|---
Alcohol, specially denatured, 39C | 40.00%
Perfume | 0.25%
Hexachlorophene | 0.15%
Water | 57.40%
Aluminum Chlorhydroxy Allantoinate | 0.20%
Propylene glycol | 2.00%

Dissolve Hexachlorophene and perfume in alcohol. Mix water and polypropylene glycol and dissolve Allantoinate in this. While stirring, slowly add water fraction to alcohol fraction. Chill, keep below 8° C. overnight and filter with about 1% filter-aid ...")

Indeed, Abe, et al, Japanese Published Patent Application No. 55-104205 published on Aug. 9, 1980 and abstracted at Chem.Abstracts, Volume 94, No. 202446 discloses:

" . . . During research for producing cosmetics effective for wound healing of cuts during shaving, chaps, and rough skin, we found that when an aloe extract was added to a cosmetic containing a surfactant, the cosmetic showed some effect for promoting healing, but when allantoin alone was added, there was no effect. On the other hand, when allantoin and an aloe extract were used together in a cosmetic containing a surfactant, the cosmetic showed increased effect on wound healing compared to the cases where aloe extract or allantoin were used alone . . . .

. . . This invention provides cosmetics for skin in which allantoin or its derivative and an aloe extract are used in the cosmetic base containing surfactants . . . .

. . . Allantoin and its derivative in this invention can be, for example, aluminum chlorohydroxy allantoinate, and aluminum dihydroxy allantoinate. Aloe extracts used with allantoin are extracted from aloe plants of lily family with polar solvents such as ethanol, methanol, aqueous alcohol, acetone, and water, or obtained by other known methods . . . . "

Table I, "Lotion Formulas" of the Abe, et al published Japanese Application states:

TABLE 1

| | LOTION FORMULAS (weight %) | | | |
|---|---|---|---|---|
| | This invention | Comparison Sample 1 | Comparison Sample 2 | Control |
| Ethanol | 40.0 | 40.0 | 40.0 | 40.0 |
| Menthol | 0.1 | 0.1 | 0.1 | 0.1 |
| Fragrance | 0.5 | 0.5 | 0.5 | 0.5 |
| Surfactant (1) | 0.7 | 0.7 | 0.7 | 0.7 |
| Aloe Extract (2) | 1.0 | 1.0 | — | — |
| Allantoin derivative (3) | 0.1 | — | — | — |
| Purified water | remaining | remaining | remaining | remaining |
| Total | 100.0 | 100.0 | 100.0 | 100.0 |
| Curve in the FIGS. | A | B | C | D |

Notes:
(1) Polyoxyethylene hardened castor oil derivative (HCO-40 by Nikko Chemicals Co.)
(2) Aloe capeliquid, 70% ethanol extract.
(3) Aluminiumchlorohydroxy allantoinate.

In Example IV of the Abe, et al, Japanese Patent Application an after-shave formulation is set forth, to wit:

| Ingredients | Weight Percent |
|---|---|
| Ethanol | 65.0% |
| Glycerine | 5.0% |
| Polyoxyethylene nonylphenyether | 2.0% |
| Aloe extract (95% Ethanol extract) | 2.0% |
| Fragrance | q.s. |
| 1-Menthol | 0.1% |
| Aluminum hydroxy allantoinate | 0.1% |
| Purified water | remaining |
| Total: | 100% |

Notwithstanding the teachings of the Abe, et al disclosure, there is still a need for a commercially acceptable single phase, clear, hydroalcoholic after-shave treatment product containing materials useful in the same manner as aloe vera taken alone or in combination with allantoin. From a marketing standpoint, the after-shave segment of the men's fragrance and treatment product market in the United States counts for approximately 40% of all the fragrance products sold. In addition, 95% of those are clear hydroalcoholic products as opposed to the opaque after-shave balms or moisturizers which are generally emulsions existing in two or more liquid phases.

Prior to our invention, nothing in the prior art disclosed or existed as a clear single-phase hydroalcoholic after-shave treatment composition containing either a combination of aloe vera and allantoin or aloe vera alone. This is due to the fact that until this point in time, the aloe extracts that were available would only produce an opaque or translucent hydroalcoholic product or would be incompatible with other required ingredients in the composition, entirely, since such prior art aloe extracts could not form a single liquid phase with such materials as perfume oils, and then be incorporated into the remainder of the after-shave composition.

Accordingly, a need exists for a clear hydroalcoholic after-shave treatment composition that provides the soothing anti-burn properties of aloe vera taken alone or taken further together with the healing properties of allantoin.

OBJECTS OF THE INVENTION

An object of our invention is to provide a clear hydroalcoholic after-shave treatment composition that provides the soothing anti-burn properties of aloe vera.

It is a further object of our invention to provide a clear hydroalcoholic after-shave treatment composition that provides the healing properties of allantoin.

It is a further object of our invention to provide a clear hydroalcoholic after-shave treatment composition that combines the soothing anti-burn properties of aloe vera with the healing properties of allantoin.

It is a further object of our invention to provide a perfume oil/aloe vera mixture that is in the liquid phase that is in the form of a single liquid phase clear composition.

DETAILED DESCRIPTION OF THE INVENTION AND DRAWINGS

Our invention is directed to a single phase clear hydroalcoholic after-shave treatment product containing aloe vera and, optionally, allantoin as well as a process for preparing same comprising the steps of:
(a) either forming
  (i) aloe vera gel; or
  (ii) a product formed by steam distilling aloe vera leaves and separating the resulting oil phase from the resulting aqueous phase;
(b) extracting the oil-miscible aloe vera fraction from the organic phase of the steam distillation product or from the aloe vera gel by intimately admixing therewith a quantity of extraction solvent and physically separating the extract phase from the raffinate phase;
(c) separating the extraction solvent from the oil-miscible aloe vera extract phase by means of fractional distillation;
(d) intimately admixing the resulting distilled oil-miscible aloe vera phase with a totally miscible perfume oil thereby forming a single phase, clear, aloe vera extract-perfume oil mixture; and
(e) admixing the resulting mixture with a polyalkylene glycol, a polyalkylene glycol alkyl ether, a quaternary ammonium salt which acts as a surfactant, a lanolin oil-polyalkylene glycol reaction product, water and, optionally, allantoin or an allantoin-aluminate complex, with the amount of water being in the range of from about 30% up to about 50% by weight of the total mixture.

Figure 1:
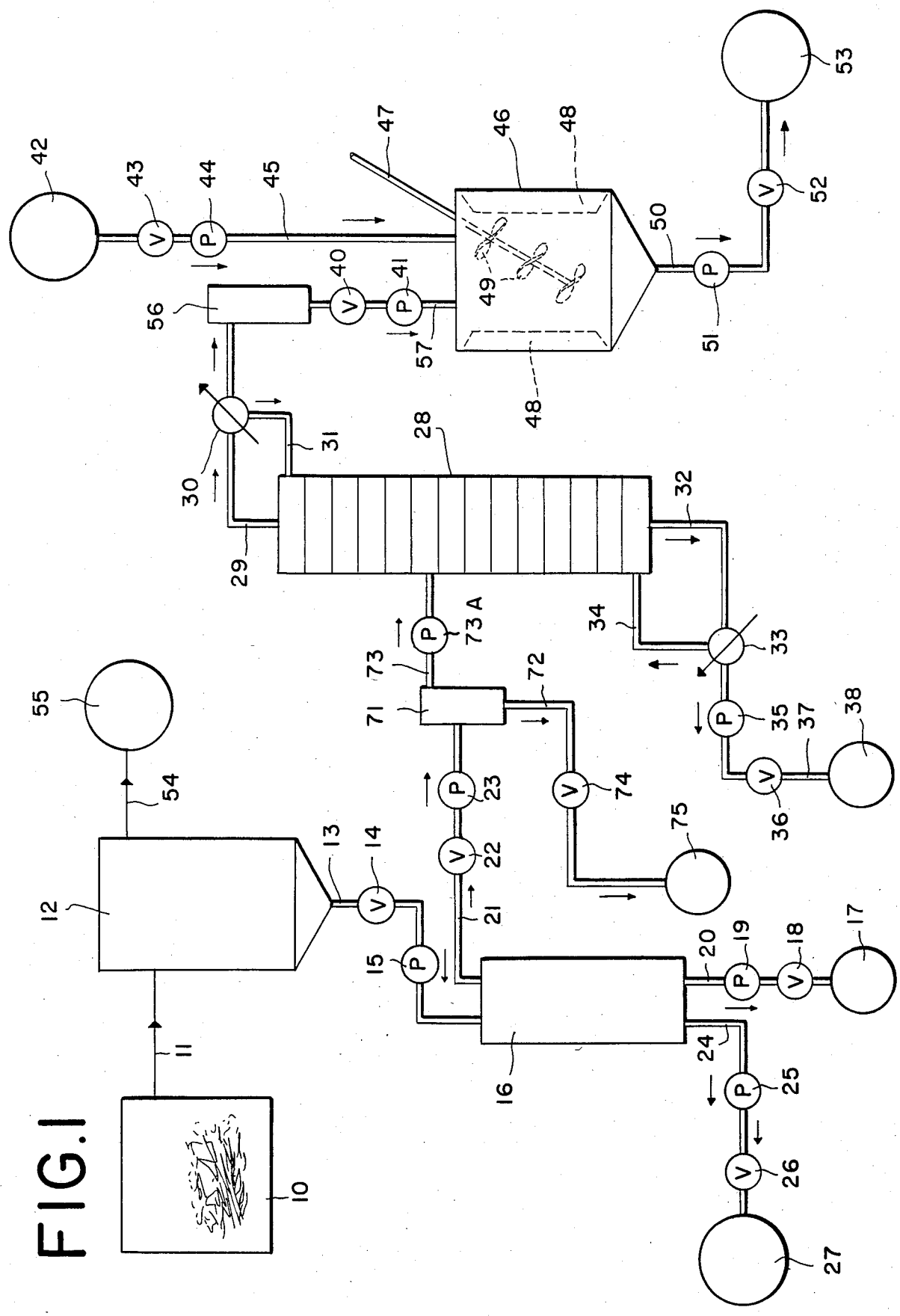
FIG. 1 is a schematic block flow diagram showing the production of a single clear phase perfume-aloe extract composition necessary as an ingredient in the formulation of the composition of our invention.
Figure 3:
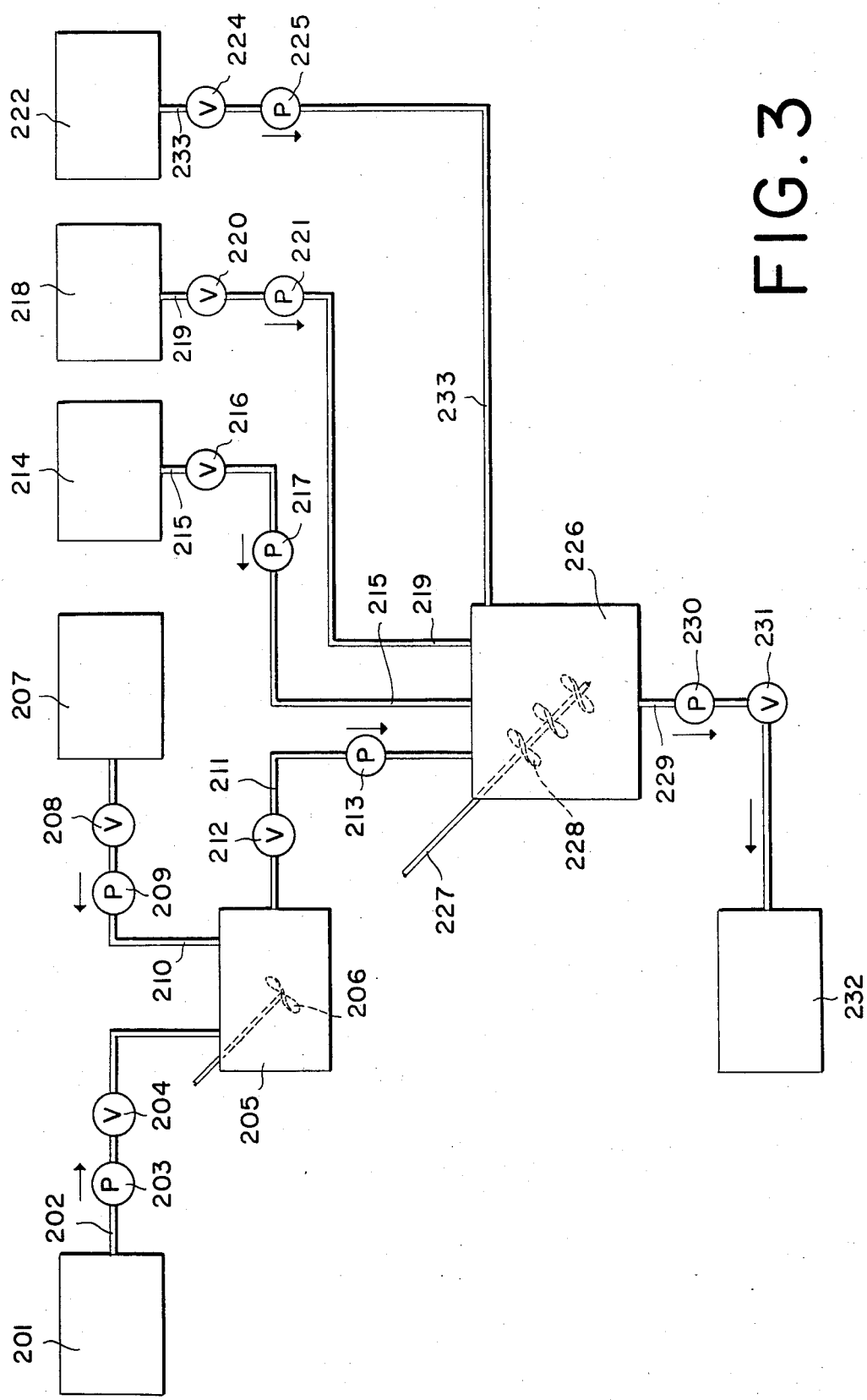
FIG. 3 is a schematic block flow diagram setting forth a process and apparatus useful for the production of the single phase clear liquid after-shave treatment product of our invention using as a starting material the clear single phase liquid mixture of perfume oil and aloe vera extract.

Thus, in FIG. 1, aloe vera gel is extracted with an oil-miscible extraction agent and the resulting two phase liquid extract is then separated into its organic phase and aqueous phase. The organic phase is distilled and the overhead distillate is condensed and combined with a compatible perfume oil. The resulting single phase clear mixture is then utilized in the composition of matter of our invention as shown in FIG. 3. Accordingly, aloe vera leaves in supply container 10 are conveyed through conveyance line 11 into the gel extracting chamber 12. The resulting gel is then pumped through line 13 past control valve 14 using pump 15 into the extraction column 16 and the leaf residue is conveyed through conveyance line 54 into residue vessel 55.

Also pumped into extraction column 16, preferably in a manner counter current to the direction of travel of the aloe vera gel, is the extraction agent fed from holding tank 17, pumped past valve 18 through line 20 using pump 19.

Examples of appropriate extraction solvents are:
1. Miglyol 812 [a hydrogenated low-boiling fraction of coconut oil];
2. Myvacet (an acetylated triglyceride); and
3. Neobee M-5 [a hydrogenated coconut oil manufactured by the Drew Chemical Company of New York, N.Y.].

The organic phase containing extraction agent and aloe vera oilsoluble extract is then pumped through line 21 past control valve 22 using pump 23 into separator 71 where any aqueous material is separated from the organic phase through line 72 past control valve 74 into holding tank 75. The oil phase is passed through line 73 through pump 73A into multi-plate distillation column 28 where the overhead fractions are distilled through line 29 using reflux cutter 30 wherein part of the distillate is refluxed back into the column through return line 31. Reflux ratios of from about 1:4 up to about 9:1 may be used. The number of theoretical plates in the fractional distillation column may vary from about 5 up to about 15. The useable overhead vapor phase material is then passed through line 39 into condenser 56 (where the vapor phase is transformed into the liquid phase) and then past control valve 40 using pump 41 through line 57 into mixing tank 46 where the resulting aloe vera oil which is miscible with perfume oil is mixed with such perfume oil, supplied from holding vessel 42 through line 45 using pump 44 past valve 43. The two materials, the perfume oil and the aloe vera-miscible extract are mixed in mixing vessel 46 preferably equipped with baffles 48 using agitator 47–49 (having agitator shaft 47 and impellers 49). The resulting mixture is then passed through line 50 using pump 51 past valve 52 into holding vessel 53 for subsequent use in the practice of our invention (as illustrated in FIG. 3). The bottoms emanating from the distillation column 28 is passed through line 32 using reboiler 33 which returns a portion of the bottoms through return line 34 into said distillation column 28. The remainder of the bottoms are passed through line 37 past valve 36 using pump 35 into holding vessel 38.

Prior to the extraction as set forth, supra, the aloe vera gel may be stabilized using the procedure of U.S. Pat. No. 4,446,131 issued on May 1, 1984, the specification for which is incorporated herein by reference.

Figure 2:
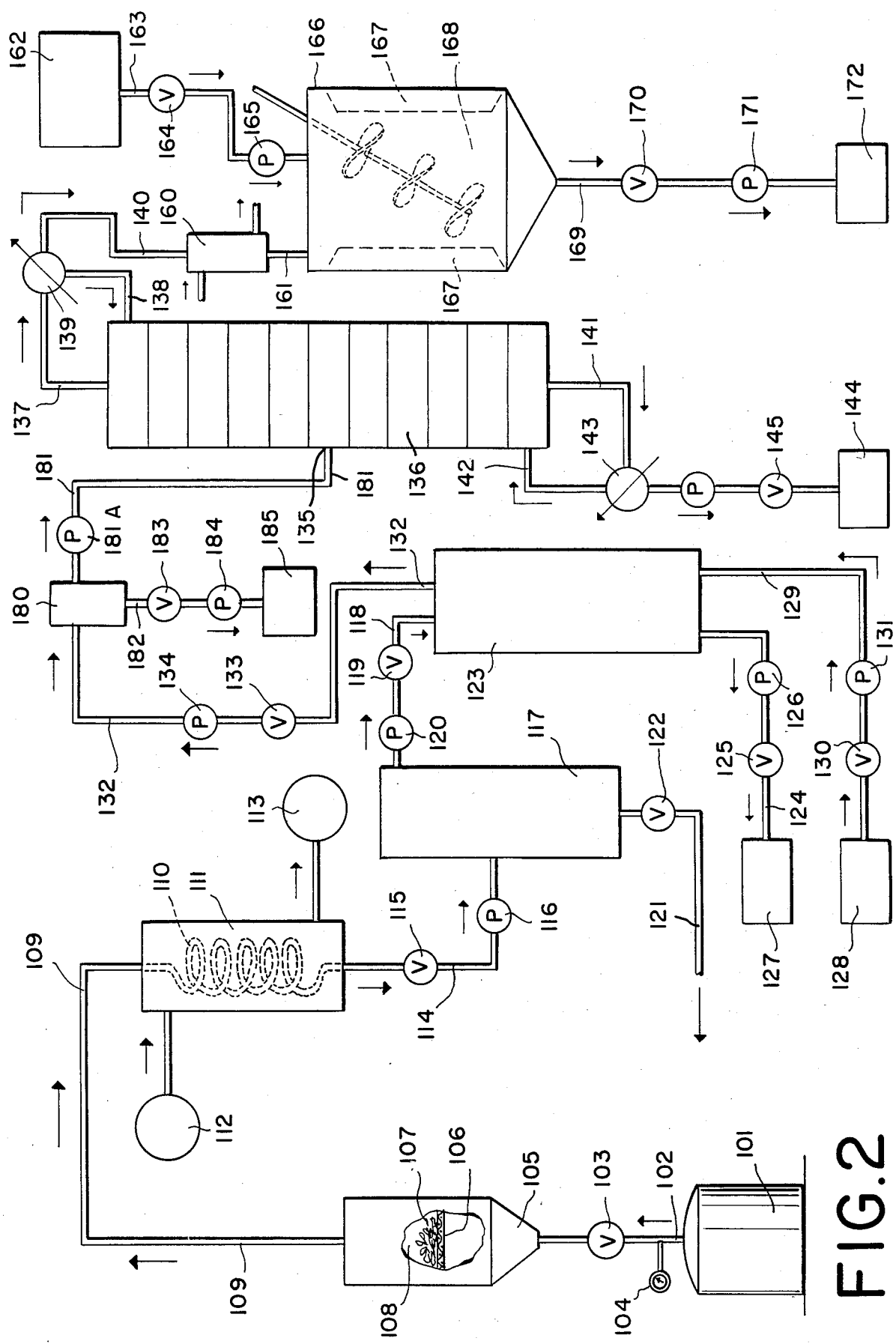
FIG. 2 is a block flow diagram of a process and apparatus useful for the production of a single phase composition containing a perfume oil and an aloe vera extract necessary as an ingredient in formulating the composition of our invention.

FIG. 2 shows the extraction of an aloe vera leaf steam distillate using an extractive distillation procedure substantially identical to the extractive distillation procedure for the aloe vera gel set forth in the block flow diagram of FIG. 1.

Thus, steam is generated at steam generator 101 and passed through line 102 past valve 103 at a pressure measured using pressure gauge 104 into steam distillation column 105. Aloe leaves 107 are held in place on screen 106 as steam is passed through the leaves into chamber 108. The resulting vapor phase mixture of steam and aloe leaf steam distillate is then passed through line 109 into water cooled condenser 111 through cooling coils 110, the condenser being cooled by water pumped from location 112 to location 113. The resulting condensed two phase mixture is then pumped through line 114 past valve 115 using pump 116 into separator 117. The lighter organic phase is then pumped through line 118 past valve 119 using pump 120 into extraction column 123 and the lower aqueous phase is removed from separator 117 past valve 122 through line 121.

Also pumped into the extraction column 123, preferably in a manner counter-current to the aloe vera leaf steam distillate organic phase is the extraction agent fed from holding tank 128, pumped past valve 130 through line 129 using pump 131.

Examples of appropriate extraction solvents are:
1. Miglyol 812 [a hydrogenated low-boiling fraction of coconut oil];
2. Myvacet (an acetylated triglyceride); and
3. Neobee M-5 [a hydrogenated coconut oil manufactured by the Drew Chemical Company of New York, N.Y.].

The organic phase extract containing extraction agent and aloe vera leaf steam distillation extract is then pumped through line 132 past control valve 133 using pump 134 into separator 180 where any aqueous material is separated from the organic phase through line 182 past control valve 183 using pump 184 into holding tank 185. The oil phase is then passed through line 181 using pump 181A into distillation column 136 at location 135. In the distillation column 136 the overhead fractions are distilled through line 137 using reflux cutter 139 wherein part of the overhead distillate is refluxed back into the column through return line 138. Reflux ratios of from about 1:4 up to about 9:1 may be used. The useable overhead vapor phase material is then passed through line 140 into condenser 160 (where the vapor phase is transformed into the liquid phase) and then through line 161 into mixing tank 166 where the resulting aloe vera oil which is miscible with perfume oil is mixed with such perfume oil supplied from holding tank 162 through line 163 past control valve 164 using pump 165. The two materials, the perfume oil and the aloe vera miscible distillate are mixed in mixing vessel 166 preferably equipped with baffles 167 using agitator means at location 168. The resulting mixture is then passed through line 169 past valve 170 using pump 171 into holding vessel 172 for subsequent use in the practice of our invention (as illustrated in FIG. 3).

The bottoms emanating from the distillation column 136 is passed through line 141 using reboiler 143 which returns a portion of the bottoms through return line 142 into distillation column 136. The remainder of the bottoms are passed into holding vessel 144 through a line equipped with control valve 145.

In place of the initial steam distillation as shown in FIG. 2 an alternative "steam" distillation procedure may be used whereby the water is admixed with the aloe leaves and the resulting slurry is subjected to batch distillation. In such case, rather than using pure water, an aqueous solvent mixture can be used. Such aqueous solvent mixture can be varied insofar as the nature of the non-aqueous solvent and the ratio of water to non-aqueous solvent are concerned. Such non-aqueous solvent may be, for example, ethyl alcohol. Furthermore, any appropriate solvent having a boiling point (at atmospheric pressure) of less than about 300° C. may be utilized. From the standpoint of economy, water or water-ethanol mixtures are preferred. A preferred ratio of water to ethanol (parts by weight) is in the range of from about 1:0.1 up to about 1:0.3. The operable ratio range of ground aloe leaves to aqueous solvent mixture or to water is from about 1:1 up to about 1:15 with a preferred range being about 1:13. Higher pressures give rise to higher temperatures of mixing, a lesser amount of required solvent:ground aloe leaves and lesser mixing periods. In addition, where a volatile solvent is used in addition to water, a low solvent to aloe leaf ratio is all that is necessary; of the order of from about 3:1 up to about 6:1 solvent:aloe leaf ratio.

The first distillation step using such slurry containing aloe leaves and aqueous solvent gives rise to several variables:
1. The total heat input per pound of ground aloe leaves;
2. The nature of the ground aloe leaf, e.g., average leaf size;
3. The pressure at which the distillation is run;
4. The time of distillation relative to the weight of ground aloe leaves;
5. The heat input rate relative to the total time of heat input;
6. The ratio in the distillation pot of the ground aloe leaves to aqueous solvent or water;
7. The rate of water or aqueous solvent input or steam input into the extractive distillation column, e.g., steam distillation column 105;
8. The number of theoretical plates in the distillation column and the number of actual plates in the distillation column, e.g., steam distillation column 105;
9. The number of beds of aloe leaves in the distillation column to be extracted;
10. The pressure drop across each of the beds of aloe leaves;
11. If several batch distillation columns (containing slurry) are used and/or if several steam distillation columns are used the number of such columns and the physical dimensions of each of the columns; and
12. The reflux ratio of the distillation column such as column 105 and other distillation columns directly associated therewith.

The most practical type of original distillation for the purpose of the instant invention is one wherein the distillate is carried immediately from a distillation pot into a condenser and the distillate is immediately and totally condensed without the use of any reflux. Nevertheless, it may be desirable when certain variation in the chemical contents of the aloe vera extract is desired, to utilize a reflux ratio (or reflux ratios where more than one column is used) up to 5:1 and, further, to utilize a distillation column (or grouping of columns) containing more than one theoretical plate.

The time, temperature and pressure of distillation are variable depending on the nature and quantity of aqueous solvent and quantity of ground aloe leaves utilized. Since it is not desired to utilize the ground aloe leaves subsequent to the distillation, conditions may be such as to extract a much larger quantity of aloe vera extract than used in distillations as disclosed in the prior art.

Preferably, where water is used as the distillation vehicle, the distillation is preferably carried out at the following ranges of conditions:

| VARIABLE | RANGE OF CONDITIONS |
|---|---|
| Pressure | 75 psia–90 psia |
| Pot temperature | 212° F.–325° F. |
| Vapor temperature | 212° F.–320° F. |
| Reflux ratio | 0–5:1 |
| Number of theoretical plates | 1–5 |
| Percent saturation of steam vapor in column effluent | 70–100% |
| Time of distillation | 0.25–3 hours |
| Total heat input | 400–5000 BTU/Pound Aloe Leaves (on dry basis) |
| Weight ratio - water-ground aloe leaf (on dry basis) | 3:1–15:1 |
| Quantity of distillate/ Pound Ground Aloe Leaf Material (on dry basis) | 0.4:1 up to 1:1 |

Where a water ethanol mixture is used as the distillation vehicle the distillation is preferably carried out at the following range of conditions:

| VARIABLE | RANGE OF CONDITIONS |
|---|---|
| Pressure | 14 psia–115 psia |
| Pot temperature | 175° F.–320° F. |
| Vapor temperature | 170° F.–320° F. |
| Weight ratio of ethanol:waters | 10:1–1:10 |
| Reflux ratios | 0–5:1 |
| Percent saturation of vapor in column effluent | 70–100% |
| Number of theoretical plates | 1–5 |
| Time of distillation | 0.25–4 Hours |
| Total heat input | 400–5000 BTU/Pound of Aloe Leaves (on dry basis) |
| Weight ratio - aqueous solution:ground aloe leaves (on dry basis) | 3:1–15:1 |

Prior to the extraction step, the distillation product may be concentrated. The concentration of the distillation product may be carried out to any practical extent desired so long as the chemical components of the aloe vera is not destroyed. It is thus preferred to proceed with the concentration at a pressure of from about 2 mm/Hg. pressure absolute up to about 0.5 atmospheres at a temperature in the range of from about 45° C. up to about 150° C.

Subsequent to the concentration step or subsequent to the actual first distillation step (e.g., steam distillation) the resulting material is extracted with a non-aqueous solvent, preferably Miglyol (a hydrogenated coconut oil) or Neobee M-5 (a hydrogenated coconut oil) as set forth, supra. The weight ratio of extract solvent to distillate is in the range of from about 1:150 up to about 1:7.5 with the preferred ratio being about 1:75 up to about 2:75. The extraction temperature may be in the range of from about 50° C. up to about 80° C. with the preferred extraction temperature range being from 20° C. up to 40° C. An extraction temperature which is too long is inefficient in that, insufficient oil soluble aloe vera is extracted from the distillate. A temperature which is too high carries problems insofar as an excessive amount of aloe vera oil soluble material volatilizes during the process. The resultant extract which exists in two phases is then separated as set forth, supra. The upper layer contains the oil soluble aloe vera which is then subjected to fractional distillation in a multi-plate distillation column as set forth, supra. The desired material is in the more volatile product distilled at a temperature in the range of from about 90° C. up to about 140° C. at from about 50 mm/Hg. pressure up to about 80 mm/Hg. pressure. The distillation is preferably carried out in a multi-plate fractional distillation column. The resulting oil soluble aloe vera is then combined with a perfume material as exemplified, infra.

Now referring to FIG. 3, the clear, single-phase liquid mixture containing aloe vera oil soluble materials and perfume oil at 201 is conveyed through line 202 using pump 203 past valve 204 into mixing vessel 205 agitated using mixture 206. From holding tank 207, alkoxylated lanolin oil (e.g., lanolin oil bonded to polypropylene glycol (12 monomeric units) and polyethylene glycol (65 monomeric units) named "LANTROLAMS" ®) is pumped through line 210 using pump 209 past valve 208 into mixing vessel 205. The resulting alkoxylated lanolin oil/aloe vera oil soluble fraction and perfume oil is then pumped through line 211 using pump 213 past valve 212 into mixing vessel 226 agitated by means of agitator 227/228 (the agitation shaft being 227 and the impeller being 228) wherein the said mixture is admixed with a mixture of water and ethanol from holding tank 214 which is passed through line 215 past control valve 216 using pump 217; quaternary ammoniom salt from holding vessel 218 being pumped through line 219 using pump 221 past valve 220 (for example, Ceraphyl 65 having the structure:

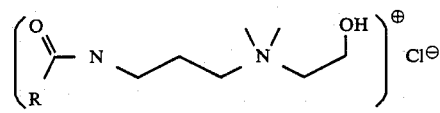

wherein R represents a Mink oil fatty acid residue) and a mixture of the following materials from holding vessel 222 through line 223 using pump 225 past valve 224, to wit:

(i) polyethylene glycol having a molecular weight of about 14,000 (denoted as "POLYOXWSRN-3000");

(ii) polypropylene glycol stearylether (containing 15 monomeric units of propoxy moieties) (denoted as Arlamol E, manufactured by the Imperial Chemical Industries Company) and having the structure:

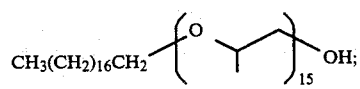

(iii) Allantoin having the structure:

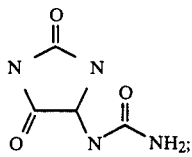

and (iv) An ultra-violet light protective agent, e.g., UVI-NUL®D-50 having the structure:

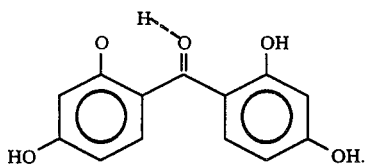

The resulting mixture is stirred for a period of about 5 hours and then pumped into appropriate containers through line 229 past valve 231 using pump 230 into the loading area 232 wherein the single-phase, clear hydroalcoholic after-shave treatment composition is prepared for marketing.

In general, the ranges of ingredients required for operability of our invention for the single-phase, clear, liquid after-shave treatment product is as follows:

| | |
|---|---|
| Ethylalcohol | From about 45 up to about 75% by weight |
| Allantoin having the structure: | From about 0.05% up to about 1.0% by weight |
| Poly lower alkylene glycol having a molecular weight of from about 8,000 up to about 20,000 | From about 2.0% up to about 5.0% |
| Quaternary ammonium salt (e.g., Ceraphyl 65 having the structure: | From about 0.2% up to about 1.0% |
| wherein R is a Mink oil fatty acid residue) | |
| Polyalkoxylated lanolin oil (e.g., lantrol which is lanolin oil bonded to polypropylene glycol (12 monomeric units) and polyethylene glycol (65 monomeric units) | From about 0.75% up to about 3.50% |
| Polyalkylene glycol alkyl ether (e.g., polypropylene glycol stearol ether such arlamol E) | From about 2.0% up to about 5.0%. |
| Polyalkylene glycol having a molecular weight of from about 8,000 up to about 20,000 (e.g., polyethylene glycol having a molecular weight of 14,000 | From about 0.05% up to about 1.0%. |
| and having the commercial name Polyox WSRN-3,000 manufactured by the Union Carbide Corporation of Danbury, Connecticut) | |
| Water | From about 20% up to about 40%. |
| Fragrance oil | From about 0.5% up to about 3.0%. |
| Aloe vera oil soluble fraction as produced (using the apparatus of FIGS. 1 or 2) | From about 0.5% up to about 3.0%. |

The following examples are given by way of illustration only and are not to be construed as limiting the scope of the instant invention. The scope of our invention is only limited by way of the claims presented at the end of the instant specification.

EXAMPLE I

To 750 grams of ground aloe vera leaf, a mixture of 750 grams of water and 150 grams of 95% ethyl alcohol is added. Under continuous stirring (at 40 rpm) the mixture is heated to 82° C. and distilled at atmospheric pressure until approximately 750 grams of distillate is obtained consisting of water, ethyl alcohol and aloe vera oil.

The distillate is then stirred at room temperature (20°–30° C.) for a period of one hour with 70 grams of Neobee M-5 (a fractionated triglyceride of reconstituted coconut oil produced by the Drew Chemical Company of Boonton, N.J. Two phases are formed and are separated. The upper layer containing substantially all of the aloe vera oil soluble fraction is then concentrated in a vacuum evaporator to one-fifth of its original volume. The resulting material is then fractionally distilled on a 15 theoretical plate Raschig ring-packed column (30′ in length×0.1′ in diameter) operated at 110° C. and 0.5 mm/Hg. pressure. The resulting overhead distillate is collected and combined with the following fragrance composition:

| Ingredients | Parts by Weight |
|---|---|
| Trans,trans-Δ-damascone | 0.5 |
| Patchouli oil East Indian | 3.2 |
| Vetiver Venezuela | 8.4 |
| Geraniol | 4.2 |
| 159 Trimethylcyclododecatriene-epoxide | 4.2 |
| β-Cyclohomocitral | 8.4 |
| Coumarin | 3.2 |

1.5 Grams of the resulting perfume/aloe vera distillate is admixed with the following materials:

| Ingredients | Parts by Weight |
|---|---|
| Ethyl alcohol | 65.00 |
| Allantoin having the structure: | 0.10 |
| Arlamol E, the stearyl ether of polypropylene glycol having the structure: | 3.50 |

| Ingredients | Parts by Weight |
|---|---|
| 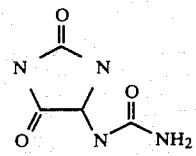 | 5 |
| Ceraphyl 65 having the structure:<br>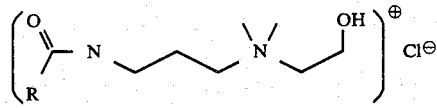<br>wherein R represents a mink oil fatty acid residue | 0.50 |
| LANTROL ® (lanolin oil/polypropylene glycol ether/polyethylene glycol ether containing 12 monomeric units of polypropylene glycol and 65 monomeric units of polyethylene glycol | 1.50 |
| Polyox WSRN-3000 1% in ethyl alcohol (polyethylene glycol having a molecular weight of 14,000 manufactured by Imperial Chemical Industries) | 0.10 |

The resulting product is a single phase clear, liquid, after-shave treatment product having an excellent aesthetically pleasing "woody" aroma and having an excellent freshening and healing properties.

What is claimed is:

1. A clear liquid phase, single phase composition consisting essentially of:
   (i) from about 45 up to about 75% by weight of ethylalcohol;
   (ii) from about 0.05% up to about 1.0% by weight of said composition of allantoin having the structure:

(iii) from about 2.0% up to about 5.0% of a poly lower alkylene glycol having a molecular weight of from about 8,000 up to about 20,000;
   (iv) from about 0.2% up to about 1.0% of a quaternary ammonium salt having the structure:

wherein R is a Mink oil fatty acid residue;
   (v) from about 0.75% up to about 3.50% of a polyalkoxylated lanolin oil which is lanolin oil bonded to 12 monomeric units of polypropylene glycol and 65 monomeric units of polyethylene glycol;
   (iv) from about 2.0% up to about 5.0% of polypropylene glycol stearol ether;
   (vii) from about 0.05% up to about 1.0% of polyalkylene glycol having a molecular weight of from about 8,000 up to about 20,000;
   (viii) from about 20% up to about 40% by weight of said mixture of water;
   (ix) from about 0.5% up to about 3.0% of a perfume oil; and
   (x) from about 0.5% up to about 3.0% of aloe vera oil soluble fraction said perfume oil being totally miscible with said aloe vera oil soluble fraction, said aloe vera oil soluble fraction produced according to the process comprising the steps of:
   (a) forming aloe vera gel or a product resulting from steam distilling aloe vera leaves and separating the resulting oil phase from the resulting aqueous phase;
   (b) extracting the oil miscible aloe vera fraction from the organic phase of the steam distillation product or from the aloe vera gel by intimately admixing therewith, a quantity of extraction solvent and physically separating the extract phase from the raffinate phase; and
   (c) separating the extraction solvent from the oil miscible aloe vera extract phase.

* * * * *